United States Patent
Nakakado (10) Patent No.: US 7,438,779 B2
(45) Date of Patent: Oct. 21, 2008

(54) METHOD OF MANUFACTURING WEARING ARTICLE

(75) Inventor: Masaki Nakakado, Osaka (JP)

(73) Assignee: Zuiko Corporation, Osaka (JP)

( * ) Notice: Subject to any disclaimer, the term of this patent is extended or adjusted under 35 U.S.C. 154(b) by 530 days.

(21) Appl. No.: 10/562,749

(22) PCT Filed: Jun. 30, 2004

(86) PCT No.: PCT/JP2004/009166

§ 371 (c)(1),
(2), (4) Date: Dec. 29, 2005

(87) PCT Pub. No.: WO2005/004776

PCT Pub. Date: Jan. 20, 2005

(65) Prior Publication Data

US 2006/0151093 A1    Jul. 13, 2006

(30) Foreign Application Priority Data

Jul. 11, 2003    (JP)    ............... 2003-195744

(51) Int. Cl.
*A61F 13/15*    (2006.01)
*B32B 37/00*    (2006.01)

(52) U.S. Cl. ............ 156/164; 156/161; 156/163; 156/229; 156/259

(58) Field of Classification Search ........ 156/160, 156/161, 163, 164, 229, 250, 259
See application file for complete search history.

(56) References Cited

U.S. PATENT DOCUMENTS

| | | | | | |
|---|---|---|---|---|---|
| 4,227,952 | A | * | 10/1980 | Sabee | ............... 156/164 |
| 4,417,938 | A | * | 11/1983 | Sigl | ............... 156/164 |
| 4,488,923 | A | * | 12/1984 | Pieniak | ............... 156/229 |
| 5,275,676 | A | * | 1/1994 | Rooyakkers et al. | ............... 156/164 |
| 6,620,276 | B1 | * | 9/2003 | Kuntze et al. | ............... 156/164 |
| 6,722,494 | B2 | | 4/2004 | Nakakado et al. | |
| 6,748,996 | B2 | | 6/2004 | Nakakado et al. | |
| 7,008,497 | B2 | * | 3/2006 | Nakakado et al. | ............... 156/229 |
| 2004/0035521 | A1 | | 2/2004 | Nakakado et al. | |

FOREIGN PATENT DOCUMENTS

| | | |
|---|---|---|
| JP | 62-69803 | 3/1987 |
| JP | 63-209936 | 8/1988 |

(Continued)

*Primary Examiner*—Jeff H Aftergut
(74) *Attorney, Agent, or Firm*—Renner, Otto, Boisselle & Sklar, LLP (57) ABSTRACT

A method for producing a worn article of the present invention comprises the steps of successively placing portions of webs W1, W2 on a plurality of pads $3_i$; slacking off the webs W1, W2 between the pads $3_i$ by shortening an interval between the pads $3_i$; placing an elastic member on the webs W1, W2 placed on the pads $3_i$ so that the elastic member extends across a slack portion Wa of each of the webs W1, W2 which is slacked off; placing an absorbent body on a non-slack portion Wp of the webs W1, W2 on the pads $3_i$ which is not slacked off; removing the slack of the webs W1, W2 by increasing the interval between the pads; and placing a sheet S1, S2 of a predetermined length on the webs W1, W2, the slack of which is removed.

16 Claims, 5 Drawing Sheets

FOREIGN PATENT DOCUMENTS

| | | |
|---|---|---|
| JP | 63-317576 | 12/1988 |
| JP | 06-197920 | 7/1994 |
| JP | 10-501195 | 2/1998 |
| JP | 2002-521091 | 7/2002 |
| JP | 2002-345889 | 12/2002 |
| WO | 95/34264 | 12/1995 |
| WO | 00/04855 | 3/2000 |
| WO | 01/44086 | 6/2001 |

* cited by examiner

FIG.5

METHOD OF MANUFACTURING WEARING ARTICLE

TECHNICAL FIELD

The present invention relates to a method for producing a disposable worn article such as a disposable diaper and disposable pants.

BACKGROUND ART

A worn article of this type includes an elastic member placed on the surface of the sheet for forming waist gathers, for example. However, such an elastic member shrinks the absorbent body and causes the absorbent body to feel stiff, thus lowering the wearing feeling.

A device is known in the art for rotating a plurality of pads about a predetermined axis while varying the velocities thereof so as to form a slack portion (see, for example, the first patent document).

the first patent document: Japanese National Phase PCT Laid-Open Publication No. 2002-521091 (pp. 1-8, FIG. 3)

DISCLOSURE OF THE INVENTION

A production method of the present invention includes the steps of: successively placing portions of a web on a plurality of pads; slacking off the web between the pads by shortening an interval between the pads; placing an elastic member on the web placed on the pads so that the elastic member extends across a slack portion of the web, which is slacked off; placing an absorbent body on a non-slack portion of the web on the pads, which is not slacked off; removing a slack of the slack portion of the web by increasing the interval between the pads; and placing a sheet of a predetermined length on the web, the slack of which is removed.

As necessary, the web, the elastic member, the absorbent body and the sheet may be bonded and layered with one another using an adhesive, or the like.

As the interval between pads is shortened while the pads are rotating and carrying the web, portions of the web between the pads are folded to form slack portions. On the other hand, other portions of the web on the pads are carried as they are without being slacked off. Then, after the elastic member is placed so as to extend across the slack portions, the interval between the pads is increased, thereby removing the slack of the web and making the slack portions unslacked. Thus, portions of the elastic member between the pads are stretched. Then, a sheet is placed on a portion of the web, the slack of which has been removed. The elastic member is interposed between this portion of the web and the sheet, thereby forming a three-layered portion including the sheet, the web and the elastic member. A contractile force from the elastic member being stretched acts upon the three-layered portion (a tensile force acts upon the elastic member itself). The contractile force makes the worn article, when worn by a wearer, fit the surface of the wearer. On the other hand, since a portion of the elastic member on a non-slack portion is not stretched, there is little shrink of the absorbent body, which is placed on the non-slack portion, thereby reducing the stiff feel caused by the absorbent body.

Specifically, in the present invention, while an elastic member is placed also on a non-slack portion, the contractile force from the elastic member on the non-slack portion is smaller than that from the elastic member on the slack portion. Thus, the shrinkage of the non-slack portion is smaller than that of the slack portion. As the absorbent body is placed on the non-slack portion with the smaller shrinkage, the stiff feel due to the absorbent body is reduced.

Each pad rotates while varying the circumferential velocity thereof in order to vary the interval between the pads. The device for shortening the interval between pads may be, for example, a rotating device described in Japanese Laid-Open Patent Publication No. 2002-345889 (Japanese Patent Application No. 2001-338061), or a device disclosed in Japanese Laid-Open Patent Publication No. 63-317576.

The pad is not limited to any type of pad as long as the pad is capable of holding and carrying a web and an absorbent body. For example, the web and the absorbent body may be sucked onto the pad by a negative air pressure, or the pad may hold the web and the absorbent body by needles or other means.

The sheet placed on the web may be a non-continuous web prepared in advance with a predetermined length. If the absorbent body is exposed between the sheets, i.e., if the sheets overlap a portion of the absorbent body with the remaining portion of the absorbent body being exposed between the sheets, the portion of the worn article where the absorbent body is placed will not be unnecessarily thick, thus improving the wearing feeling, and the absorptive property will not be lowered.

A production method of the present invention may include, as web forming steps, the steps of: dividing a web into a first web including a first side edge and a second web including a second side edge; shifting a phase of the first web in a flow direction and that of the second web from each other; and separating the first web and the second web from each other so as to increase a distance from the first side edge of the first web to the second side edge of the second web. With the provision of these steps, a space is formed in advance between the first web and the second web, thereby reducing the amount of web to be discarded when making a leg hole, thus providing an advantage of reducing the cutting loss of the web.

Such a production method may include the steps of: successively placing portions of the first web and portions of the second web on a plurality of pads; slacking off the first and second webs between the pads by shortening an interval between the pads; placing an elastic member on each of the first and second webs placed on the pads so that the elastic member extends across a slack portion of the respective web, which is slacked off; placing an absorbent body so that the absorbent body extends between non-slack portions of the first and second webs on the pads, which are not slacked off; removing a slack of the slack portion of the first and second webs by increasing the interval between the pads; and placing a sheet of a predetermined length on each of the first and second webs, the slack of which is removed.

The step of shifting the phases of the first web and the second web from each other and the step of separating the first web and the second web from each other may be performed simultaneously, or the first and second webs may be separated from each other after shifting the phases of the first web and the second web from each other. Conversely, the phases of the first and second webs may be shifted from each other after the first and second webs are separated from each other to a certain degree or more, or after the first and second webs are separated from each other completely.

The elastic member may be a rubber thread, or the like, wound around a bobbin in advance, or may be an elastic hotmelt resin. Where an elastic hotmelt is used as the elastic member, the interval (pitch) in the width direction between elastic members discharged in the form of threads can be set to be much smaller than that when rubber threads are used.

Moreover, in such a case, there is no restriction on the number of threads to be put in, as there is no need to place bobbins, unlike in the case where rubber threads, or the like, are used as the elastic member.

Instead of discharging an elastic hotmelt in the form of threads, an elastic hotmelt may be discharged in a planar (film) form.

The present production method may further include a step of making a leg hole in the web.

BRIEF DESCRIPTION OF THE DRAWINGS

FIG. 3(*a*) is a perspective view showing a web on which elastic members are stacked, and FIG. 3(*b*) is a schematic side view of the device showing a portion of the device near an attachment unit.

FIGS. 4(*a*) and 4(*b*) are plan views showing a web production step and a sheet production step.

FIGS. 5(*a*), 5(*b*), 5(*c*), 5(*d*) and 5(*e*) are plan views showing a worn article production step.

DESCRIPTION OF THE REFERENCE NUMERALS $3_i$: Pad
C: Absorbent body
F: Elastic member
Lh: Leg hole
S, S1, S2: Sheet
W: Web
W1: First web
W1*s*: First side edge portion
W2: Second web
W2*s*: Second side edge portion
Wa: Slack portion
Wp: Non-slack portion

BEST MODE FOR CARRYING OUT THE INVENTION

An embodiment of the present invention will now be described with reference to the drawings.

Figure 1:
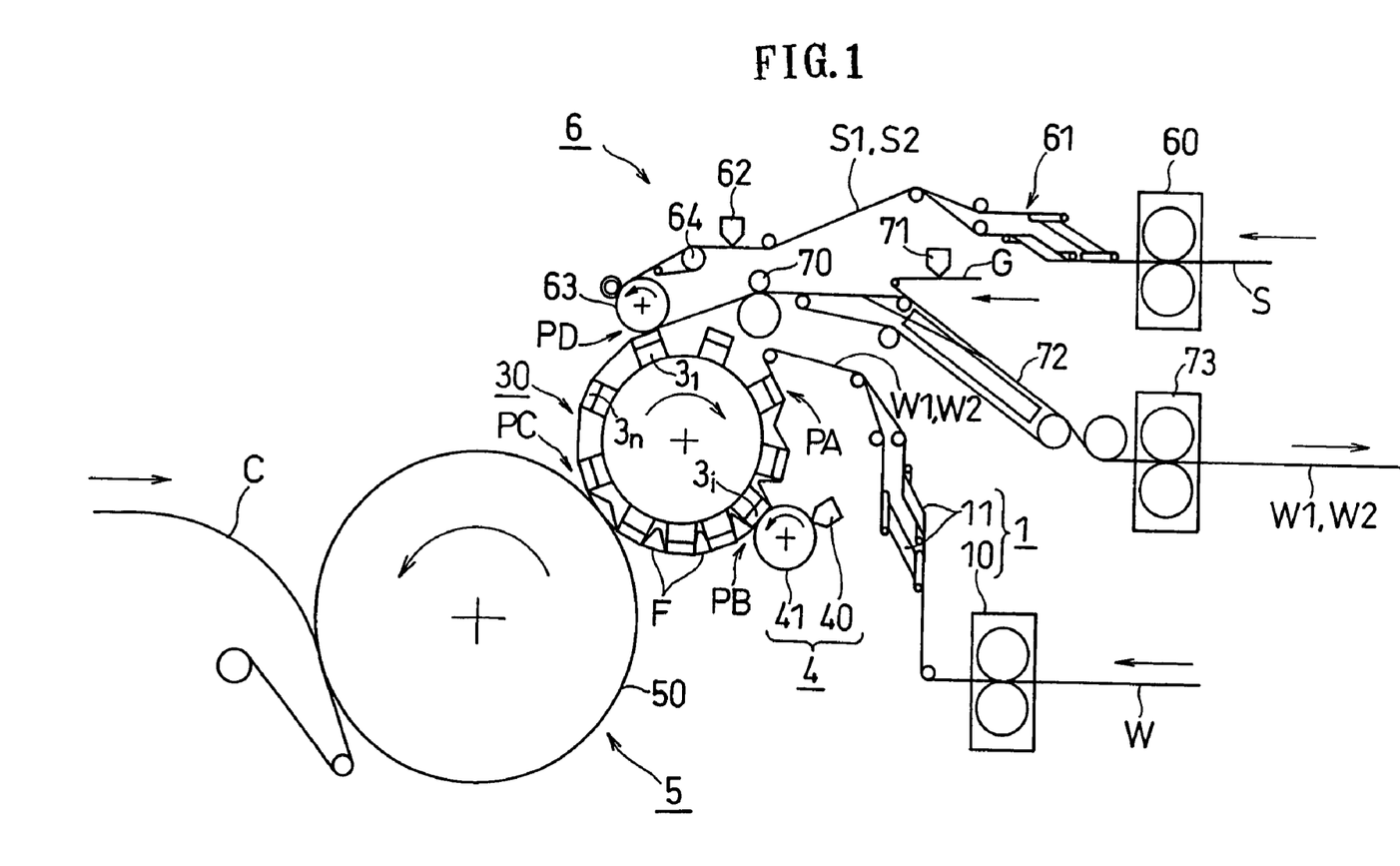
FIG. 1 is a side layout view showing a device for producing a worn article according to an embodiment of the present invention.

A production device for producing a worn article shown in FIG. 1 is a device for placing an elastic member F, an absorbent body C, the sheet S, etc., on a web W.

For example, the production device shown in FIG. 1 includes a web processing device 1, a rotating device 30, an elastic member placement device 4, an absorbent body placement device 5, and a sheet placement device 6. Various processing devices 70 to 73 to be described later may be provided downstream of the sheet placement device 6.

Figure 4:
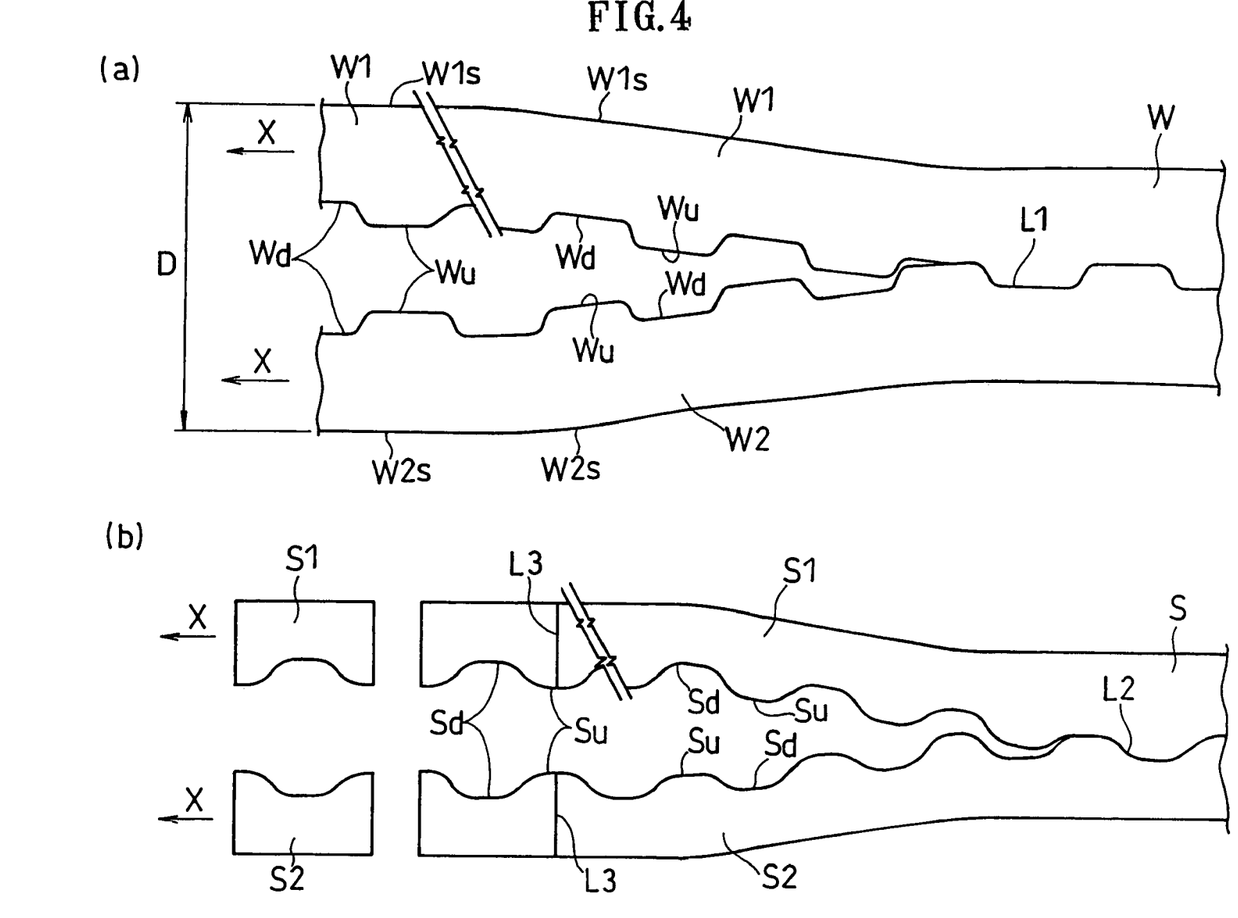

Web Processing Device 1:

The web processing device 1 includes a web cutter 10 and a phase-changing device 11. FIG. 4(*a*) is a plan view showing a web processing step. As shown in FIG. 4(*a*), the web W supplied from upstream is cut along a cut-off line L1 by the web cutter 10 (FIG. 1) so as to be divided into a first web W1 including a first side edge W1*s* and a second web W2 including a second side edge W2*s*. Through this cutting process, the web is divided into the webs W1 and W2 having an alternating series of protruding portions Wu and depressed portions Wd at the first and second side edges W1*s* and W2*s*, respectively.

The side edges W1*s* and W2*s* are the side edges of the web W opposing each other in the width direction.

The phase-changing device 11 of FIG. 1 moves one continuous web W1 and the other continuous web W2 away from each other in the width direction to widen the distance of the webs while shifting the phase of one web W1 in the flow direction from that of the other web W2 by ½ the pitch. Thus, the webs W1 and W2 are carried with their protruding portions Wu opposing each other and their depressed portions Wd opposing each other. That is, by the phase-changing device 11, the web W is carried with the phases of the webs W1 and W2 being shifted from each other so that the webs W1 and W2 are placed generally in a line symmetry with each other with respect to the carry direction (flow direction) X.

The phases of the webs W1 and W2 may be shifted from each other by setting the path for one of the web W1 and the web W2 to be longer than the other by ½ the pitch, as shown in FIG. 1, or by passing one web around a dummy roll so that the web is lagged behind the other web.

For the widening of the distance between the webs, the distance D from the side edge W1*s* of one web W1 to the side edge W2*s* of the other web W2 need to be increased, but both of the webs W1 and W2 need not necessarily be moved away from each other.

Figure 2:
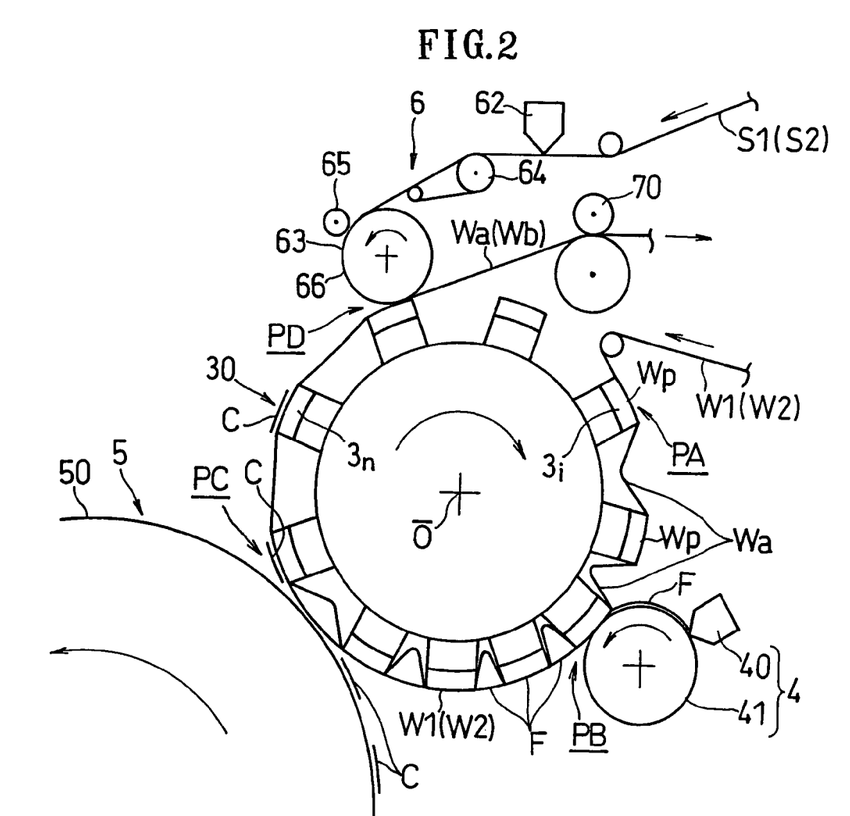
FIG. 2 is a schematic side view showing a portion of the device near a rotating device.
Figure 3:
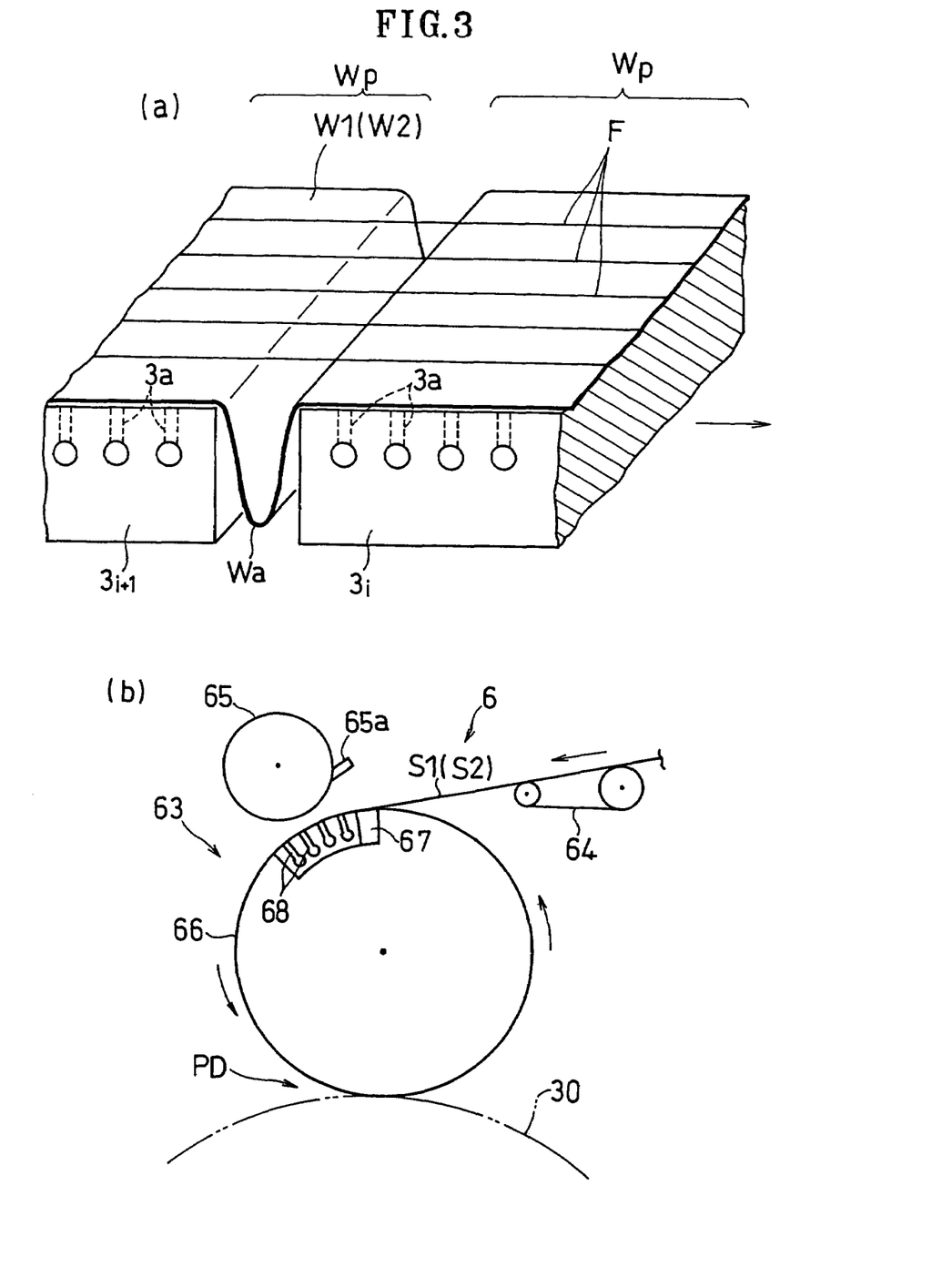

Rotating Device 30:

The webs W1 and W2 are supplied from the web processing device 1 to the rotating device 30. As shown in FIG. 2, the rotating device 30 includes a plurality of pads $3_i$ capable of carrying the webs W1 and W2 while sucking the webs W1 and W2 thereon. As shown in FIG. 3(*a*), a plurality of suction holes 3*a* for sucking the webs W1 and W2 are provided on the surface of each pad $3_i$.

The pads $3_i$ shown in FIG. 2 pick up the webs W1 and W2 and suck the webs thereon at a pickup position PA. The pad $3_i$ sucks the protruding portion Wu (FIG. 4(*a*)) a portion of the webs W1 and W2. In this process, the pad $3_i$ picks up the webs W1 and W2 while rotating at substantially the same velocity as the supply velocity of the webs W1 and W2. This is not to damage the webs W1 and W2.

After the pickup, the pad $3_i$ starts decelerating. Due to the deceleration of the pad $3_i$ shown in FIG. 3(*a*), the interval between the pad $3_i$ and the following pad $3_{i+1}$ is shortened, thereby slacking off the webs W1 and W2 between the pads and thus forming a slack portion Wa in the webs W1 and W2. Thus, the slack portion Wa slacked off toward the center O of the rotating device 30 shown in FIG. 2 is formed in the webs W1 and W2.

It is preferred that the rotating device 30 is provided with a directing section so that the slack portion Wa is reliably slacked off toward the center O of the rotating device 30.

The directing section may be, for example, an air-blowing mechanism, a mechanism for thrusting the slack portion Wa of the web toward the center of rotation O of the rotating device 30, or a mechanism for sucking, by vacuum, the web W toward the center of rotation O of the rotating device 30. Where the directing section is an air-blowing mechanism, a single directing section may be provided, or a plurality of directing sections may be provided. Where the directing section is a mechanism for thrusting the slack portion, a single directing section may be provided, or a plurality of directing sections may be provided. By providing a plurality of directing sections, the slack portion Wa can reliably be folded in toward the center of rotation O of the rotating device 30.

Alternatively, the slack portion Wa may be let to fall into a shape dented toward the center of rotation O of the rotating device 30 by the weight of the webs W1 and W2 themselves.

The rotating device for forming the slack portion Wa is not limited to the rotating device 30 as described above, but may alternatively be a device described in International Publication WO2001/044086 (Japanese Patent Application No. 2001-545183), for example. Note that the elastic member F need be placed so as to extend across the slack portions Wa of the webs W1 and W2 as will be described later, but the webs W1 and W2 do not have to be folded completely.

Elastic Member Placement Device 4:

The elastic member placement device 4 of FIG. 1 places the elastic member F on the webs W1 and W2 placed on the pads $3_j$ so that the elastic member F extends across the slack portions Wa of the web. For example, the elastic member placement device 4 includes a supply device 40 and a chill roll 41. A melted resin (elastic member) F discharged from the supply device 40 is chilled by the chill roll 41, and then the elastic member F on the chill roll 41 is placed on the webs W1 and W2 at an elastic member placement position PB. Therefore, as shown in FIG. 3(a), the elastic member F is placed so as to extend across the slack portions Wa of the webs W1 and W2 and only on non-slack portions Wp and Wp, which are not slacked off, of the webs W1 and W2 on two adjacent pads $3_j$ ($3_{j+1}$). In other words, the elastic member F is placed so as to extend across a slack portion Wa of the webs W1 and W2 by extending between a non-slack portion Wp that is upstream of the slack portion Wa in the flow direction and another non-slack portion Wp that is downstream of the slack portion Wa in the flow direction.

While only several threads of the elastic member F are placed in FIG. 3(a) for the sake of simplicity, more elastic member threads than shown in this figure may be placed. In such a case, the elastic member F may be discharged from the supply device 40 of FIG. 2 in the form of fine threads. Alternatively, the elastic member F may be discharged from the supply device 40 in the form of a film. The gun for discharging the elastic member F may be of a bead type, a spiral type, a curtain type, a spray type, etc. Moreover, the elastic member F does not have to be placed continuously over the pads, but may alternatively be placed intermittently in the flow direction. Then, it is possible to produce a worn article in which basically no elastic member F is placed under the absorbent body C.

The chill roll 41 of FIG. 2 may be a porous roll. Where the chill roll 41 is a porous roll, it may employ a structure in which an air is discharged from inside the chill roll 41 to the outside through the pores. The air makes it unlikely that a hotmelt resin adheres to the roll. Moreover, as an air exits a pore of the porous roll, the volume of the air increases to deprive the roll of heat. Thus, the hotmelt resin can be chilled. The porous roll may be made by sintering beads of stainless steel, etc.

Alternatively, grooves, or the like, may be formed on the chill roll 41 so that a resin is shaped by the grooves. For example, grooves of a mesh pattern (e.g., a lattice pattern) may be formed on the chill roll 41, so that an elastic member of a mesh pattern is formed by applying a hotmelt resin on the grooves of the chill roll 41 by a coater, or the like.

Alternatively, the cooling device of the chill roll 41 may be based on water cooling.

Alternatively, the elastic member F may be applied directly on the webs W1 and W2, not via the chill roll 41.

Note that the elastic hotmelt resin may be a resin whose primary component is a thermoplastic polymer resin, and containing a tackifier, a viscosity modifier, an antioxidant, a thermal stabilizer, an ultraviolet radiation absorbent, a filler, a plasticizer, etc. The elastic hotmelt may be a kneaded, non-volatile adhesive with no solvent, having such a composition.

The thermoplastic polymer resin may be a polyurethane resin, an olefin resin [EVA (Ethylene Vinyl Acetate copolymer), APAO (Amorphous PolyAlpha Olefin)], a rubber resin [SIS (Styrene Isoprene Styrene copolymer), SBS (Styrene Butadiene Styrene copolymer), SEBS (Styrene Ethylene Butylene Styrene copolymer), SEPS (Styrene Ethylene Propylene Styrene copolymer)], a polyamide resin, or a polyester resin. One of these resins may be used solely, or some of them may be blended together.

Absorbent Body Placement Device 5:

The absorbent body placement device 5 shown in FIG. 2 is a device for placing the absorbent body C on the webs W1 and W2, and includes a transfer drum 50, for example. After the placement of the elastic member F, the pad 3 starts accelerating, and the absorbent body C is transferred from the transfer drum 50 at an absorbent body placement position PC.

Figure 5:
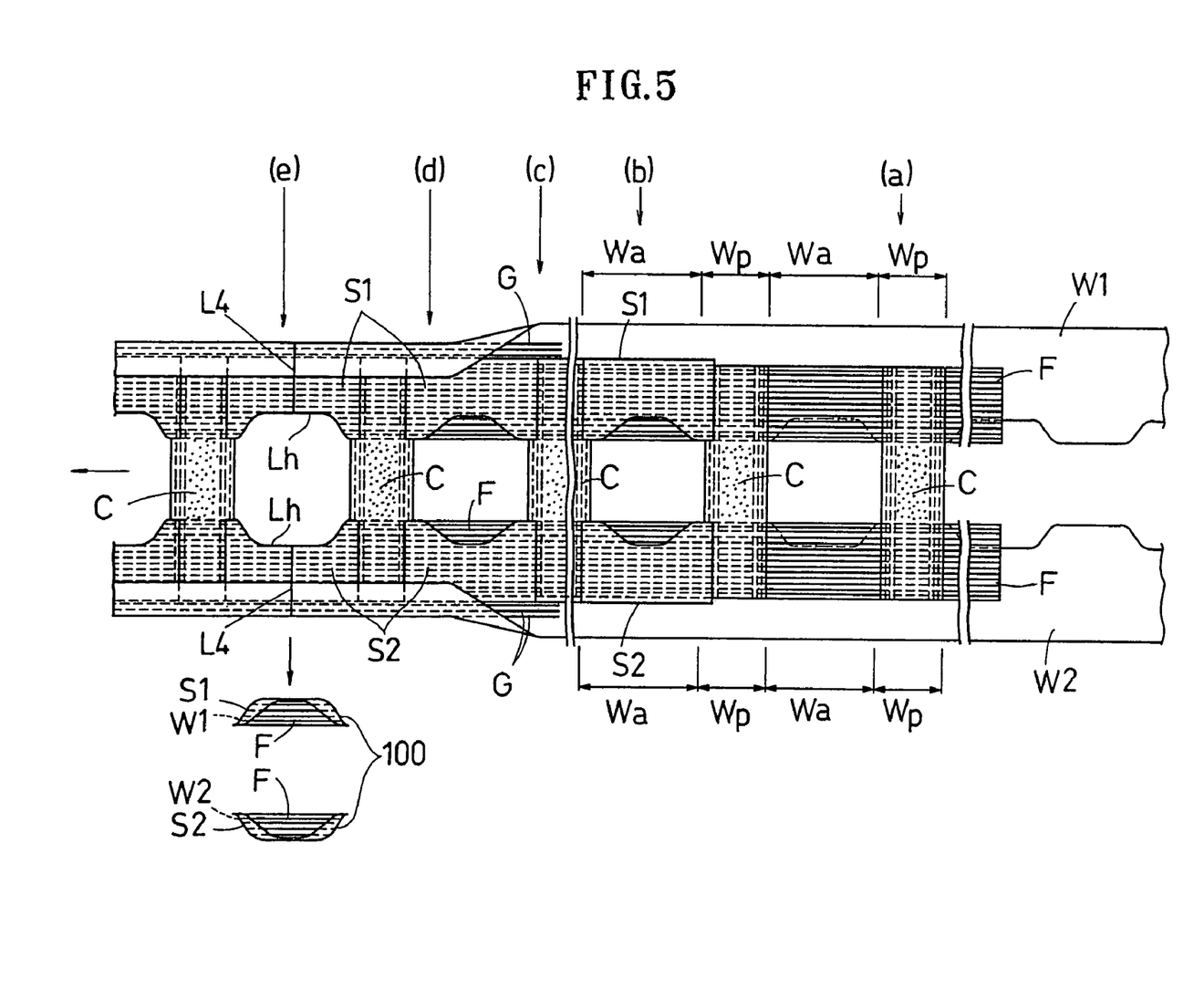

FIG. 5 is a plan view showing a web processing step. As shown in FIG. 5(a), the absorbent body C is placed by the absorbent body placement device 5 (FIG. 2) so as to extend across two non-slack portions Wp and Wp of the first and second webs W1 and W2 on the pad $3_j$ (FIG. 2). The absorbent body C is placed so that the end portions thereof are respectively on the pair of webs W1 and W2. The non-slack portions Wp are formed in a portion of the web upstream of the slack portion Wa in the flow direction and in another portion of the web downstream of the slack portion Wa in the flow direction.

At the absorbent body placement position PC of FIG. 2, the velocity of the pad $3_j$ is set to be a generally constant velocity that is equal to or near the circumferential velocity of the transfer drum 50. Thus, the pad $3_j$ moves at a generally constant circumferential velocity that is equal to the circumferential velocity of the transfer drum 50 at least while the pad $3_j$ is set to be in contact with the transfer drum 50 via the absorbent body C therebetween or at least while the transfer drum 50 is placing the absorbent body C on the non-slack portions Wp of the webs W1 and W2. In other words, the pad $3_j$ moves at a constant circumferential velocity from when the webs W1 and W2 on the pad $3_j$ starts receiving the absorbent body C until the webs W1 and W2 finishes receiving the absorbent body C. This prevents the webs W1 and W2 and the absorbent body C from being displaced from each other due to a velocity difference, and the absorbent body C can therefore be handed over precisely to a predetermined position of the webs W1 and W2.

Sheet Placement Device 6:

The sheet placement device 6 is a device for forming sheets S1 and S2, and placing the sheets S1 and S2 on at least a portion of the slack portion Wa on which the elastic member F has been placed as shown in FIG. 5. So-called "gathers" are formed in a portion where the webs W1 and W2, the elastic member F and the sheets S1 and S2 are stacked together.

The sheet placement device 6 shown in FIG. 1 includes a sheet cutter 60, a phase-changing device 61, an adhesive application device 62, and a sheet attachment unit 63.

As shown in FIG. 4(b), the sheet cutter 60 cuts a sheet S along a cut-off line L2 so as to divide the sheet S into a first sheet S1 and a second sheet S2. As with the first and second webs W1 and W2, the sheet is divided into the sheets S1 and S2 having an alternating series of protruding portions Su and depressed portions Sd.

The phase-changing device 61 of FIG. 1 widens the distance between two sheets S1 and S2 formed by above division while shifting the phase of one sheet S1 in the flow direction from that of the other sheet S2 by ½ the pitch, as with the web W. Thus, the sheets S1 and S2 of FIG. 4(b) are carried with their depressed portions Sd opposing each other and their protruding portions Su opposing each other. Therefore, by the phase-changing device 11, the sheet S is carried with the phases of the sheets S1 and S2 being shifted from each other and the sheets S1 and S2 being placed generally in a line symmetry with each other with respect to the carry direction (flow direction) X.

The application device 62 of FIG. 1 applies an adhesive on the sheets S1 and S2.

Attachment Unit 63:

The sheet attachment unit 63 of FIG. 3(b) includes a conveyor 64 for forwarding the sheets S1 and S2 at a predetermined velocity, a cutter roll 65 having at least one blade for cutting the sheets S1 and S2, and a carrying roll 66 for carrying the cut sheets S1 and S2.

For example, the conveyor 64 may continuously forward the sheets S1 and S2 or may intermittently forward the sheets S1 and S2.

While the carrying roll 66 rotates, sucking sections 68 thereof suck the sheets S1 and S2 thereon. At this time, the surface of the carrying roll 66 and the sheets S1 and S2 are rubbed against each other. Where the sheets S1 and S2 are forwarded continuously, the circumferential velocity of the carrying roll 66 is greater than the velocity at which the conveyor 64 feeds the sheets S1 and S2. Also where the sheets S1 and S2 are forwarded intermittently, the circumferential velocity of the carrying roll 66 is greater than the velocity at which the conveyor 64 feeds the sheets S1 and S2, in terms of average velocities.

The sheets S1 and S2 are cut at a predetermined length by being nipped between at least one blade 65a of the cutter roll 65 and a blade rest (anvil) 67 of the carrying roll 66. The blade rest 67 is not provided with suction holes since it receives the blade 65a. The length of the sucking section 68 in the rotation direction is set to be greater than the length at which the sheets S1 and S2 are cut. When the blade 65a and the blade rest 67 come into contact with each other via the sheets S1 and S2 therebetween, the circumferential velocity of the tip of the blade 65a is about equal to or greater than the circumferential velocity of the carrying roll 66. After the sheets S1 and S2 are cut by the cutter roll 65, the circumferential velocity of the carrying roll 66 may be increased.

After the sheets S1 and S2 are cut by the cutter roll 65 along a cut-off line L3 (FIG. 4(b)), the cut-off piece is separated due to the velocity difference between the conveyor 64 and the carrying roll 66, and is placed on the webs W1 and W2 at a sheet transferring position PD.

At the sheet transferring position PD of FIG. 1, the velocity of the pad $3_i$ is set to be a generally constant velocity that is equal to or near the circumferential velocity of the carrying roll 66. The sheets S1 and S2 are placed on the webs W1 and W2 when or after the circumferential velocity of the pad $3_i$ is at maximum near the sheet transferring position PD of FIG. 2. This is because if the sheets S1 and S2 are picked up before the circumferential velocity of the pad $3_i$ reaches the maximum velocity, the interval between adjacent pads increases after the pickup, which may damage the sheets S1 and S2 or crease the sheets S1 and S2.

As the circumferential velocity of the pad $3_i$ reaches the maximum velocity, the distance between pads increases, whereby the slack of the slack portion Wa is removed and the elastic member F is stretched, and the sheets S1 and S2 are placed on the slack portion Wa as shown in FIG. 5(b). The sheets S1 and S2 may be placed so that a portion thereof overlaps the absorbent body C. After the placement of the sheets S1 and S2, an air is blown out of the suction holes 3a of FIG. 3(a), and the webs W1 and W2 are released from the pad $3_i$ and passed downstream.

As shown in FIG. 1, nip rolls 70, an application device 71, a folder 72 and a leg hole cutter 73 are provided downstream of the rotating device 30.

The nip rolls 70 press, from above and below, the webs W1 and W2 on which various members as described above are layered, thereby bonding together the webs W1 and W2, the elastic member F, the absorbent body C and the sheets S1 and S2.

The application device 71 applies an adhesive on a waist rubber G. As shown in FIG. 5(c), the waist rubber G with the adhesive applied thereon is placed on the webs W1 and W2. Then, as shown in FIG. 5(d), the folder 72 (FIG. 1) folds the outside ends of the webs W1 and W2. Then, the leg hole cutter 73 (FIG. 1) makes a leg hole Lh in the webs W1 and W2 as shown in FIG. 5(e). Thus, the leg hole cutter 73 (FIG. 1) cuts off portions of the webs W1 and W2, the elastic member F and the sheets S1 and S2 between the absorbent bodies C and C. The cut-off pieces 100 are discarded. Then, the stack including the webs W1 and W2, etc., is cut along a cut-off line L4 into individual pairs of pants.

Production Method:

As shown in FIG. 1, the web W continuously supplied from upstream is divided by the web cutter 10 into the first web W1 and the second web W2 (FIG. 4(a)). After the division, the phase-changing device 11 widens the distance between the webs W1 and W2 and shifts the phases thereof from each other.

Then, the webs W1 and W2 are supplied from the web processing device 1 to the rotating device 30, and portions of the webs W1 and W2 are successively placed on the pads $3_i$. The pad $3_i$ of the rotating device 30 shown in FIG. 2 sucks the webs W1 and W2 thereon at the pickup position PA and then decelerates. The deceleration of the pad $3_i$ shortens the interval between pads and slacks off the web between the pads, thereby forming the slack portions Wa in the webs W1 and W2 and forming the non-slack portions Wp upstream and downstream of the slack portion Wa.

Then, at the elastic member placement position PB, the elastic member placement device 4 places the elastic member F on the webs W1 and W2 placed on the pad $3_i$ so that the elastic member F extends across the slack portion Wa of the webs W1 and W2 (FIG. 3(a)). After the placement of the elastic member F, the pad $3_i$ is accelerated.

After the placement of the elastic member F, the transfer drum 50 successively places the absorbent bodies C at the absorbent body placement position PC so that the absorbent body C extends between two non-slack portions Wp and Wp, which are not slacked off, of the webs W1 and W2 on the pad $3_i$ (FIG. 5(a)).

In the sheet placement device 6 shown in FIG. 1, the sheet S is formed. The sheet S continuously supplied from upstream is divided by the sheet cutter 60 into the first sheet S1 and the second sheet S2 (FIG. 4(b)). After the division, the phase-changing device 61 widens the distance between the sheets S1 and S2 and shifts the phases thereof from each other.

After an adhesive is applied thereon by the application device 62, the sheets S1 and S2 are cut off by the attachment unit 63 along the cut-off line L3 (FIG. 4(b)). The cut-off sheets S1 and S2 are placed on the webs W1 and W2 on the rotating device 30 at the sheet transferring position PD shown in FIG. 2.

At the sheet transferring position PD, the circumferential velocity of the pad $3_i$ reaches the maximum velocity and the interval between pads increases, whereby the slack of the slack portion Wa is removed and the elastic member F is stretched. The sheets S1 and S2 of a predetermined length are placed on the webs W1 and W2, the slack of which has been removed (FIG. 5(b)). After the placement of the sheets S1 and S2, the webs W1 and W2 are released from the pad $3_i$ and passed downstream.

The pad $3_i$ continues to rotate to reach the pickup position PA, where it newly picks up the webs W1 and W2 and starts decelerating.

The stack including the webs W1 and W2, which has been moved off the pad $3_i$, is compressed between the nip rolls 70 shown in FIG. 1, thereby bonding together the webs W1 and W2, the elastic member F, the absorbent body C and the sheets S1 and S2. Thus, the elastic member F is interposed between the webs W1 and W2 and the sheets S1 and S2, whereby the stack stretches/shrinks as the elastic member F stretches/shrinks. Thus, gathers are formed.

Then, the waist rubber G on which an adhesive has been applied by the application device 71 is placed on the webs W1 and W2 (FIG. 5(c)). After the placement, the lateral ends of the webs W1 and W2 are folded by the folder 72 (FIG. 5(d)). Then, the leg hole Lh is made by the leg hole cutter 73 in the stack including the webs W1 and W2 (FIG. 5(e)). Then, the stack including the webs W1 and W2 is carried downstream, and is cut along the cut-off line L4 into individual pairs of pants.

INDUSTRIAL APPLICABILITY

The present invention is applicable to the production of a disposable worn article, such as a disposable diaper and disposable pants, including an absorbent body.

The invention claimed is:

1. A method for producing a worn article, comprising the steps of:
successively placing portions of a web on a plurality of pads;
slacking off the web between the pads by shortening an interval between the pads;
placing an elastic member on the web placed on the pads so that the elastic member extends across a slack portion of the web, which is slacked off;
placing an absorbent body on a non-slack portion of the web on the pads, which is not slacked off;
removing a slack of the slack portion of the web by increasing the interval between the pads; and
placing a sheet of a predetermined length on the web, the slack of which is removed.

2. A method for producing a worn article according to claim 1, wherein the elastic member is an elastic hotmelt.

3. A method for producing a worn article according to claim 1, further comprising a step of making a leg hole in the web.

4. A method for producing a worn article according to claim 2, further comprising a step of making a leg hole in the web.

5. A method for producing a worn article by carrying a web in a predetermined flow direction while holding the web by a plurality of pads, comprising the steps of:
successively placing portions of the web on the pads being apart from one another in the flow direction, whereby the web is placed extending over the pads;
slacking off the web between the pads by shortening an interval between the pads, thus forming a slack portion in the web that is slacked off and forming a upstream non-slack portion upstream of the slack portion of the web in the flow direction and a downstream non-slack portion downstream of the slack portion of the web in the flow direction;
placing an elastic member between the upstream non-slack portion and the downstream non-slack portion so that the elastic member extends across the slack portion of the web;
placing an absorbent body on each of the non-slack portions;
removing a slack of the slack portion by increasing the interval between the pads; and
placing a sheet of a predetermined length on the web, the slack of which is removed.

6. A method for producing a worn article according to claim 5, wherein the elastic member is an elastic hotmelt.

7. A method for producing a worn article according to claim 6, further comprising a step of making a leg hole in the web.

8. A method for producing a worn article according to claim 5, further comprising a step of making a leg hole in the web.

9. A method for producing a worn article, comprising the steps of:
dividing a web into a first web including a first side edge portion and a second web including a second side edge portion;
separating the first web and the second web from each other so as to increase a distance from the first side edge portion of the first web to the second side edge portion of the second web;
shifting a phase of the first web and that of the second web from each other;
successively placing portions of the first web and portions of the second web on a plurality of pads;
slacking off the first and second webs between the pads by shortening an interval between the pads;
placing an elastic member on each of the first and second webs placed on the pads so that the elastic member extends across a slack portion of the respective web, which is slacked off;
placing an absorbent body so that the absorbent body extends between non- slack portions of the first and second webs on the pads, which are not slacked off;
removing a slack of the slack portion of the first and second webs by increasing the interval between the pads; and
placing a sheet of a predetermined length on each of the first and second webs, the slack of which is removed.

10. A method for producing a worn article according to claim 9, wherein the elastic member is an elastic hotmelt.

11. A method for producing a worn article according to claim 10, further comprising a step of making a leg hole in the web.

12. A method for producing a worn article according to claim 9, further comprising a step of making a leg hole in the web.

13. A method for producing a worn article by carrying a web in a predetermined flow direction while holding the web by a plurality of pads, comprising the steps of:
dividing a web having a first side edge portion and a second side edge portion extending along the flow direction into a first web including the first side edge portion and a second web including the second side edge portion;
separating the first web and the second web from each other so as to increase a distance from the first side edge portion of the first web to the second side edge portion of the second web;
shifting a phase of the first web in the flow direction and that of the second web from each other;
successively placing portions of the first web and portions of the second web on the pads being apart from one another in the flow direction, whereby each of the first and second webs is placed extending over the pads;

slacking off the first and second webs between the pads by shortening an interval between the pads, thus forming a slack portion in each of the first and second webs that is slacked off and forming a upstream non-slack portion upstream of the slack portion of each of the first web and the second web in the flow direction and a downstream non-slack portion downstream of the slack portion of each of the first web and the second web in the flow direction;

placing an elastic member between the upstream non-slack portion and the downstream non-slack portion of each of the first web and the second web so that the elastic member extends across the slack portion of each of the first web and the second web;

placing an absorbent body so that the absorbent body extends between the upstream non-slack portion of the first web and that of the second web;

placing another absorbent body so that the absorbent body extends between the downstream non-slack portion of the first web and that of the second web;

removing a slack of the slack portions of the first and second webs by increasing the interval between the pads; and placing a sheet of a predetermined length on each of the first and second webs, the slack of which is removed.

14. A method for producing a worn article according to claim 13, wherein the elastic member is an elastic hotmelt.

15. A method for producing a worn article according to claim 14, further comprising a step of making a leg hole in the web.

16. A method for producing a worn article according to claim 13, further comprising a step of making a leg hole in the web.

* * * * *